(12) United States Patent
Samset et al.

(10) Patent No.: US 9,842,427 B2
(45) Date of Patent: Dec. 12, 2017

(54) METHODS AND SYSTEMS FOR VISUALIZATION OF FLOW JETS

(71) Applicant: General Electric Company, Schenectady, NY (US)

(72) Inventors: Eigil Samset, Oppegard (NO); Andreas Heimdal, Oslo (NO)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/007,031

(22) Filed: Jan. 26, 2016

(65) Prior Publication Data

US 2017/0213380 A1    Jul. 27, 2017

(51) Int. Cl.

| | |
|---|---|
| *G06T 17/00* | (2006.01) |
| *G06T 15/08* | (2011.01) |
| *G06T 17/20* | (2006.01) |
| *A61B 8/06* | (2006.01) |
| *A61B 8/08* | (2006.01) |
| *A61B 8/00* | (2006.01) |

(52) U.S. Cl.
CPC .............. *G06T 15/08* (2013.01); *A61B 8/065* (2013.01); *A61B 8/463* (2013.01); *A61B 8/5207* (2013.01); *A61B 8/5223* (2013.01); *G06T 17/20* (2013.01)

(58) Field of Classification Search
None
See application file for complete search history.

(56) References Cited

U.S. PATENT DOCUMENTS

| | | | | |
|---|---|---|---|---|
| 6,219,059 | B1* | 4/2001 | Argiro | G06T 11/00 345/424 |
| 2006/0256914 | A1* | 11/2006 | Might | G01N 23/04 378/57 |
| 2007/0255138 | A1* | 11/2007 | Kristofferson | A61B 8/06 600/443 |
| 2009/0015587 | A1* | 1/2009 | Hashimoto | A61B 8/06 345/424 |

* cited by examiner

*Primary Examiner* — Martin Mushambo
(74) *Attorney, Agent, or Firm* — McCoy Russell LLP

(57) ABSTRACT

Methods and systems are provided for calculating flow transparency values that improve the visualization of turbulent blood flow with an ultrasound imaging system. In one embodiment, a method comprises calculating transparency values for a plurality of voxels based on a variance value and a velocity value of each voxel and a time corresponding to acquisition of each voxel, and rendering an image with the calculated transparency values applied to the plurality of voxels. In this way, the visualization of turbulent blood flow can be tailored to the dynamics of the blood flow, thereby enabling an improved diagnostic accuracy.

20 Claims, 4 Drawing Sheets

METHODS AND SYSTEMS FOR VISUALIZATION OF FLOW JETS

FIELD

Embodiments of the subject matter disclosed herein relate to diagnostic ultrasound systems, and more particularly, to controlling the visualization of blood flow.

BACKGROUND

Measurement of blood flow in the heart and vessels using the Doppler effect is well known. Whereas the amplitude of the reflected waves is employed to produce grayscale images of the tissues, the frequency shift of the reflected waves may be used to measure the velocity of the reflecting scatterers from tissue or blood. Color flow images are produced by superimposing a color image of the velocity of moving material, such as blood, over the grayscale anatomical image. The measured velocity of flow at each voxel determines its color.

Diagnosing and assessing turbulent blood flow through a vessel can be challenging with current ultrasound systems. Normal blood flow may obscure or otherwise make it difficult to visualize part or all of a turbulent flow jet when displayed on a display or monitor. The blood flow jets that occur within the heart during mitral valve or tricuspid valve regurgitations typically have velocities higher than the Nyquist velocity when using color Doppler. Due to aliasing, high velocity blood flow may be detected and displayed incorrectly as low velocity, and thus is not accurately measured.

Previous approaches to overcoming the above problem include adjusting the transparency of flow voxels based on the velocity and variance (or turbulence) of each voxel. However, even in such approaches, noise or artifacts can still be misidentified as jets while short jet bursts may be overlooked or obscured.

BRIEF DESCRIPTION

In one embodiment, a method comprises calculating transparency values for a plurality of voxels based on a variance value and a velocity value of each voxel and a time corresponding to acquisition of each voxel, and rendering an image with the calculated transparency values applied to the plurality of voxels. In this way, the visualization of turbulent blood flow can be tailored to the dynamics of the blood flow, thereby enabling an improved diagnostic accuracy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
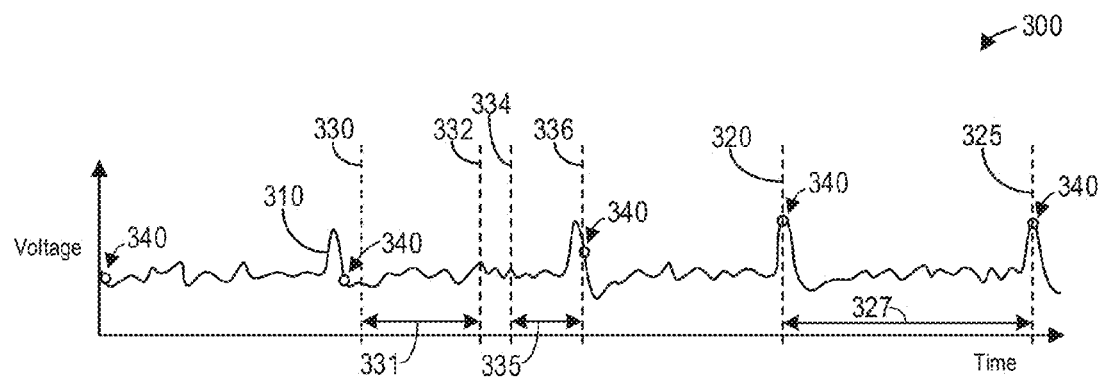
FIG. 3 shows a graph illustrating a method for selecting temporal periods of interest using an echocardiogram according to an embodiment of the invention.
Figure 4:
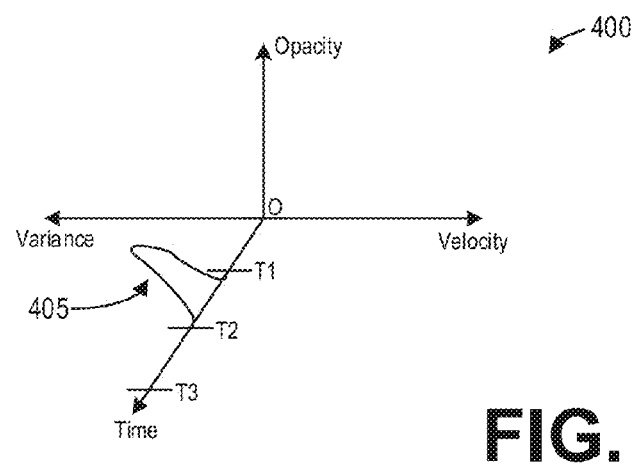
FIG. 4 shows a graph illustrating a transparency transfer function according to an embodiment of the invention.

The following description relates to various embodiments of ultrasound imaging techniques. In particular, methods and systems for calculating flow transparency values are provided that improve the visualization of turbulent blood flow with an ultrasound imaging system. For example, an ultrasound imaging system such as the system depicted in FIG. 1 may acquire and process ultrasound data to generate color Doppler images. To visualize turbulent blood flow, the ultrasound imaging system may carry out a method, such as the method depicted in FIG. 2, wherein transparency values for each voxel within a volume of ultrasound data are calculated based on variables including but not limited to velocity, variance, time, and space. For example, in order to focus on a particular phenomenon during the cardiac cycle, the visualization of blood flow may be limited to portions of the cardiac cycle, as depicted in FIG. 3. The transparency values are calculated using a multivariable transparency transfer function, an example of which is depicted in FIG. 4. As shown in the unprocessed ultrasound image of FIG. 5 and the processed ultrasound image of FIG. 6, such an approach enables an operator to visualize flow dynamics of interest while rendering transparent any blood flow that may obscure said dynamics.

It should be appreciated that color Doppler images described herein may comprise two-dimensional images, three-dimensional images, and/or four-dimensional images (e.g., color Doppler images may comprise a plurality of images corresponding to different acquisition times, and may be displayed sequentially at a particular frame rate). In turn, the systems and methods described herein may be used to generate two-, three-, or four-dimensional color Doppler images with improved flow visualization.

Though an ultrasound system is described by way of example, it should be understood that the present techniques may also be useful when applied to images acquired using other imaging modalities, such as computed tomography (CT), tomosynthesis, MM, C-arm angiography, and so forth. The present discussion of an ultrasound imaging modality is provided merely as an example of one suitable imaging modality.

Figure 1:
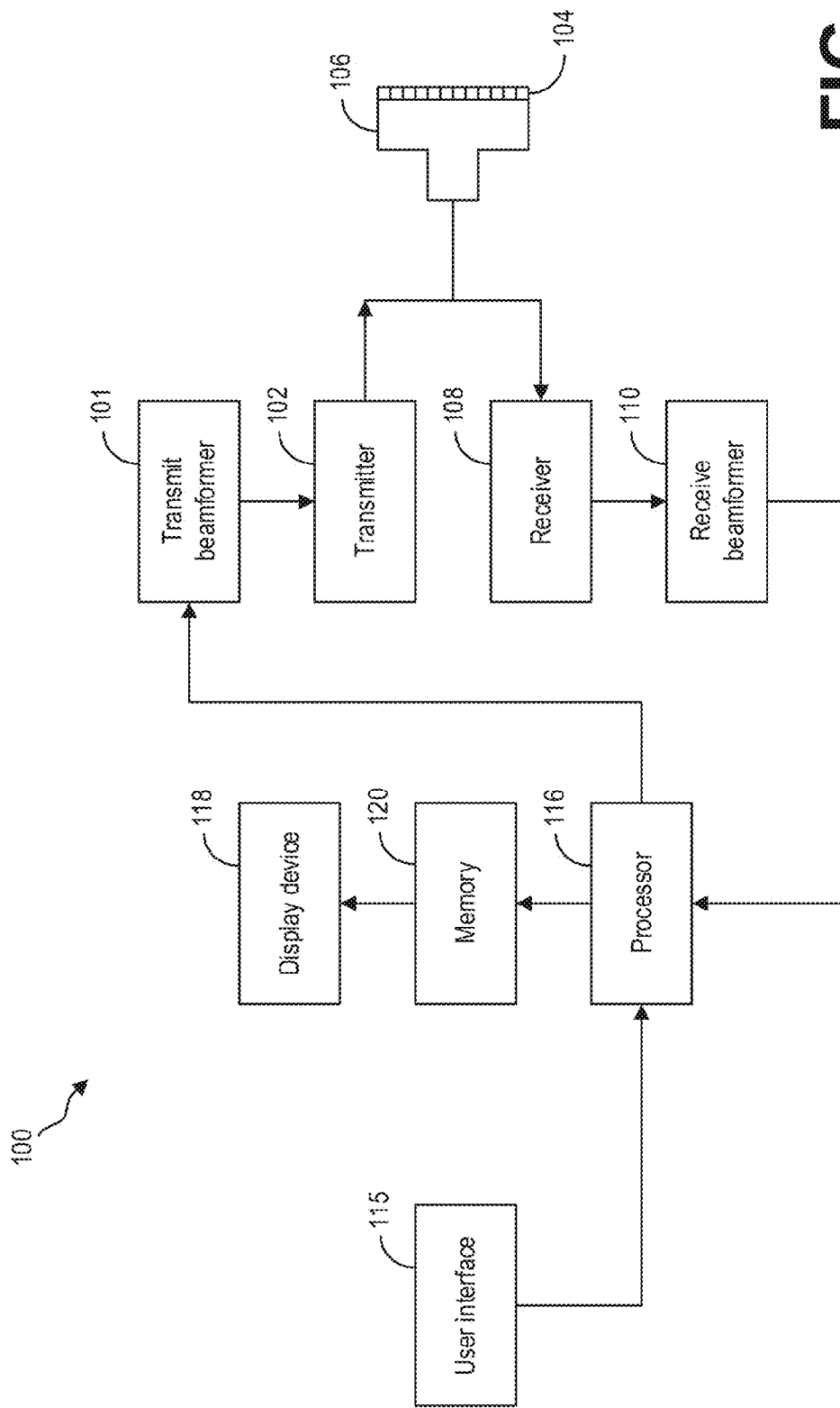
FIG. 1 shows an ultrasound imaging system according to an embodiment of the invention.

FIG. 1 is a schematic diagram of an ultrasound imaging system 100 in accordance with an embodiment of the invention. The ultrasound imaging system 100 includes a transmit beamformer 101 and a transmitter 102 that drive elements 104 within a transducer array, or probe, 106 to emit pulsed ultrasonic signals into a body (not shown).

According to an embodiment, the transducer array 106 may be a one-dimensional transducer array probe. However, in some embodiments, the transducer array 106 may be a two-dimensional matrix transducer array probe.

Still referring to FIG. 1, the pulsed ultrasonic signals are back-scattered from structures in the body, like blood cells or muscular tissue, to produce echoes that return to the elements 104. The echoes are converted into electrical signals by the elements 104 and the electrical signals are received by a receiver 108. The electrical signals representing the received echoes are passed through a receive beamformer 110 that outputs ultrasound data.

According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106.

The terms "scan" or "scanning" may also be used in this disclosure to refer to acquiring data through the process of transmitting and receiving ultrasound signals. The term "data" may be used in this disclosure to refer to either one or more datasets acquired with an ultrasound imaging system.

A user interface 115 may be used to control operation of the ultrasound imaging system 100, including to control the input of patient data, to change a scanning or display parameter, and the like. The user interface 115 may include one or more of a rotary, a mouse, a keyboard, a trackball, hard keys linked to specific actions, soft keys that may be configured to control different functions, a graphical user interface displayed on the display device 118, and so on.

The ultrasound imaging system 100 also includes a processor 116 to control the transmit beamformer 101, the transmitter 102, the receiver 108, and the receive beamformer 110. The processor 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118.

The processor 116 may include a central processor (CPU) according to an embodiment. According to other embodiments, the processor 116 may include other electronic components capable of carrying out processing functions, including but not limited to a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain.

The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described above. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds' worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

As described further herein, the ultrasound imaging system 100 enables a method for calculating flow transparency values based on multiple variables, including but not limited to velocity, variance, time, and space. A transparency transfer function defined as a function of these variables will allow transparency of the rendered color flow to be adjusted so that jet bursts of varying length will stand out in the visualization.

Figure 2:
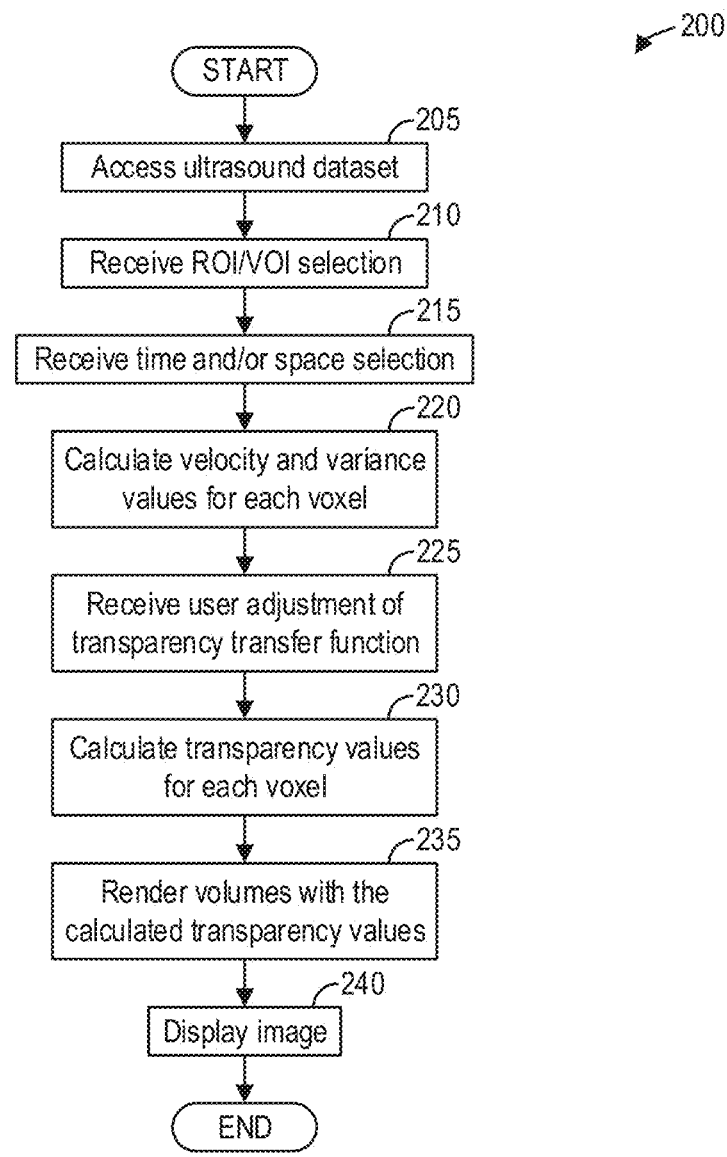
FIG. 2 shows a high-level flow chart illustrating an example method for calculating flow transparency values according to an embodiment of the invention.

FIG. 2 shows a high-level flow chart illustrating an example method 200 for visualizing ultrasound data in accordance with the present disclosure. In particular, method 200 relates to calculating transparency values for voxels based on a multi-dimensional transparency transfer function. Method 200 is described herein with regard to color Doppler ultrasound imaging mode, though it should be appreciated that the method may be applied to other imaging modes and modalities without departing from the scope of the present disclosure. Further, method 200 may be carried out using the components and systems depicted in FIG. 1. For example, method 200 may be carried out by processor 116 in combination with one or more hardware components and may be stored as executable instructions in memory 120. However, it should be appreciated that the method 200 may be applied to other systems without departing from the scope of the present disclosure.

Method 200 may begin at 205. At 205, method 200 includes accessing an ultrasound dataset. The ultrasound dataset comprises a collection of ultrasound data acquired during at least one ultrasound scan to be processed according to the methods described herein. In some examples, the ultrasound dataset may be accessed in real-time as the data comprising the ultrasound dataset is acquired. In this way, method 200 may be carried out in real-time during a scan. In other examples, the ultrasound dataset may be accessed after acquisition of the data comprising the ultrasound dataset. In this way, ultrasound data may be post-processed in accordance with method 200.

At 210, method 200 may include receiving a region-of-interest (ROI) or volume-of-interest (VOI) selection. The ROI or VOI selection may be performed by an operator of the ultrasound system via a user interface, such as the user interface 115. The ROI or VOI may include such anatomy as the mitral valve or the tricuspid valve, for example. Optionally, the ROI or VOI may comprise the entire scanned volume of data.

At 215, method 200 may include receiving a time and/or space selection. A time selection may comprise at least one indication of a time to be used as an input for the transparency transfer function. For example, a time selection may comprise an indication of a start time and an indication of an end time. The ultrasound dataset may be time-indexed, and the time selection may correspond to particular frames within the ultrasound dataset. In some examples, the ultrasound dataset may be temporally correlated to an echocardiogram (ECG) for the patient, wherein the ECG is measured during the ultrasound scan. In such examples, the time selection may correspond to one or more times in the ECG.

As an illustrative and non-limiting example, FIG. 3 shows a graph 300 illustrating an example method for selecting temporal periods of interest using an echocardiogram (ECG) 310. ECG 310 may be measured during the ultrasound scan and may be temporally correlated with the ultrasound data. In some examples, the ECG 310 may be displayed, for example via display device 118, to the operator, who may select, for example via the user interface 115, a start time 320 and an end time 325 to establish a time window 327. As described further herein, the start time 320 and the end time 325 may be input to the transparency transfer function, which is then constrained to performing transparency calculations within the time window 327. As a non-limiting example, flow voxels outside of the time window may be set to full transparency by default.

In other examples, notable cardiac events (e.g., valve openings, valve closings, and so on) may be automatically identified in the ECG 310. Such automatically identified events may be denoted in the ECG 310 via a plurality of markers 340. In such examples, the operator may manually select one or more of the markers 340 to establish a start time 320 and/or an end time 325. Specific events or intervals may also be automatically identified in the ECG 310 through event indicators. For example, indicators may be displayed to an operator to indicate the temporal position of events such as an aortic valve opening (AVO) event 330, an aortic valve closing (AVC) event 332, a mitral valve opening (MVO) event 334, a mitral valve closing (MVC) event 336, and so on, and additional indicators may be displayed to indicate corresponding intervals such as systole 331 and diastole 335. Such indicators may be displayed within one cardiac cycle (as depicted), or throughout the ECG 310 for each cycle.

In this way, in some examples, the operator may select particular events or intervals rather than times. For example, the operator may indicate that he or she wishes to limit the transparency calculation to when the mitral valve is open, and so a mitral valve open event (e.g., at 334) may be selected as the start time and a mitral valve close event (e.g., at 336) may be selected as the end time. As mentioned above, the method may automatically determine when such events or intervals occur, for example based on the ECG and/or the ultrasound data.

Similarly, for example in both cardiac and non-cardiac imaging scenarios, the operator may manually establish a time window by inputting a start time and an end time based on the ultrasound data alone. In this way, time may be used as an input to the transparency transfer function without the use of an ECG 310.

Alternatively or additionally, the time window may be automatically established based on one or more of the ultrasound data, the Doppler data, the ECG, other recordings, and so on.

In examples wherein the ultrasound data is acquired over a plurality of cycles (e.g., in cardiac imaging), a time window selected within a single cycle may be automatically applied to each cycle.

Returning to FIG. 2, regarding an optional space selection, the operator may select particular spatial regions or locations within the ultrasound volume. To that end, the operator may manually select a spatial region (e.g., by drawing the spatial region via the user interface) in one frame within the ROI. The boundaries delineating the selected spatial regions may be correlated to specific voxels which are tracked from frame-to-frame in the ultrasound data (e.g., using a tissue tracking algorithm). Additionally or alternatively, the operator may input a desired region by name, and the method may automatically identify the spatial region within the ultrasound data by use of a dictionary or lookup table. It should be appreciated that the methods for performing a space selection described above are non-limiting examples, and that other techniques for selecting a spatial region within an image may be used.

The space selection may then be used as an input to the transparency transfer function such that the transparency calculations occur only within the selected region. In the absence of a space selection input by a user, the entire ROI/VOI received at 210 may be used as a space selection by default. Thus, it should be appreciated that in some examples, the transparency transfer function may be adjusted based on a sub-region or sub-volume of the ROI or VOI.

As another example, when a segmented model of the heart that is being imaged is available, this model may be used to provide anatomical input to the transfer function. Such knowledge, such as the location of the left ventricular endocardial border, may be used to limit the visualization of flow to this region. Such knowledge may also be used, for example, to only show flow around the aortic and/or mitral valve (or other valves of interest).

After receiving the time and/or space selection, method 200 proceeds to 220. At 220, method 200 includes calculating velocity and variance values for each voxel. In color Doppler ultrasound imaging, each voxel represents blood flow or tissue, such as a point on an artery wall or a heart valve. Voxels representing blood flow are herein referred to as voxels or flow voxels, and voxels representing tissue are referred to as tissue voxels. Each flow voxel within the volume of data has associated parameters which may be used to describe and/or classify the voxel, such as variance, velocity, and amplitude. Velocity in color flow may also be referred to as frequency. Conventionally, variance is proportional to the square of the bandwidth of the Doppler signal, with unit frequency squared or velocity squared. Voxels that contain blood regions with large velocity gradients will show a large value of the variance parameter. Additionally, because of a physical mechanism referred to as the transit time effect, voxels representing regions with large velocities will also have a large variance. Therefore, velocity and variance are related such that a flow voxel having high velocity also has high variance. Variance may also be referred to as bandwidth or turbulence.

At 225, method 200 may include receiving a user selection and/or adjustment of the transparency transfer function. The transparency transfer function comprises a multivariable function that defines the relationship between a transparency value and multiple inputs, including but not limited to velocity, variance, time, and space. In some examples, a default transparency transfer function may be selected by default based on one or more selections, including but not limited to the ROI selection, the time selection, and the space selection. Such default transparency functions may be linear, piecewise linear, or nonlinear. In some examples, the operator or user may select a transparency transfer function from a plurality of pre-configured transparency transfer functions.

Further, the operator may perform adjustments to the transparency transfer function. Specifically, the operator may define or adjust the transparency values for each variable individually or in combination. For example, the operator may be interested in high velocities, and so would adjust the transparency transfer function such that voxels with high velocities are opaque while voxels with low velocities are transparent.

As an illustrative and non-limiting example, FIG. 4 shows a graph 400 illustrating an example transparency transfer function 405 which defines the relationship between variance, velocity, and time to opacity/transparency. The time markers T1, T2, and T3 on the time axis indicate valve events (e.g., opening, closing). Thus, as an illustrative example, an operator may select times T1 and T2 as a begin time and a start time, respectively, in order to study mitral regurgitation which may occur between those two valve events. The transparency level is determined along the opacity axis, wherein the opacity increases from fully transparent at the origin O to fully opaque away from the origin. Similarly, the variance levels and velocity levels increase along the respective axes away from the origin.

In some examples, the transparency transfer function 405 may be displayed to the operator, via a display device such as display device 118, who may in turn adjust, via a user interface such as user interface 115, the shape of the transparency transfer function 405 by use of a cursor or other another graphical editing tool as desired. In other examples, the adjustment may be accomplished manually through the user interface 115 by entering a variable input such as a number between zero and one. Alternatively, a user-define transparency level may be set by a protocol or based on user preference.

As depicted, the transparency transfer function maps the multiple variables (e.g., variance, velocity, time, and so on) to a transparency/opacity value. It should be appreciated that by including time as a variable, two voxels with the same variance and velocity values but acquired at different times within the time window may have different transparency values. This understanding is also applied to examples wherein spatial positions are included as input variables to the transparency transfer function. For example, two voxels with the same variance and velocity values acquired at the same time but in different spatial positions within the volume may have different transparency values.

Referring again to FIG. 2, method 200 proceeds to 230 after receiving a user adjustment of the transparency transfer function. At 230, method 200 includes calculating transparency values for each voxel. In some examples, the method calculates transparency values for each voxel with the transparency transfer function which, as described above, may be based on velocity, variance, and time, such as the flow transparency value is equal to h(variance, velocity, time). Thus, the transparency transfer function in such examples has three variables.

In other examples, the method calculates transparency values for each voxel with the transparency transfer function which may be based on velocity, variance, time, and space, such that the flow transparency value is equal to h(variance, velocity, time, space). Since space may be indicated in three-dimensional space (e.g., Cartesian coordinates x, y, z, or other coordinate systems), the transparency transfer function in such examples has six variables.

At 235, method 200 may include rendering volumes with the calculated flow transparency values. Volume rendering methods, steps, and the like which are known in the art may be used. It should be appreciated that the volume rendering may generate a single image or a plurality of images corresponding to different times (which may be displayed as a video at a certain frame rate). For example, the transparency transfer function, since it includes time as a variable, enables the method to generate a single image which combines data acquired over time. In other words, the transparency transfer function enables a static display of three-dimensional blood flow throughout the cardiac cycle (or throughout at least a portion of the cardiac cycle) by integrating flow information over time (using said transfer function) to generate a static three-dimensional image of the blood flow footprint. Further, by taking time into account, the transparency transfer function may be tailored to the flow dynamics relevant to a particular clinical task (e.g., since the transfer function may take valve event times as input), thus creating a clear and robust mechanism for jet visualization.

At 240, method 200 may include displaying the image or plurality of images using a display device such as display device 118 based on at least the flow transparency values which correspond to displayed transparency levels. Method 200 may then end. However, in some examples the method may optionally return to 225, wherein the operator may further adjust the user-defined transparency level to increase or decrease the level of transparency for some or all of the flow voxels. The method then recalculates the transparency values, renders the volumes with the calculated transparency values, and displays the volume-rendered image(s).

Figure 5:
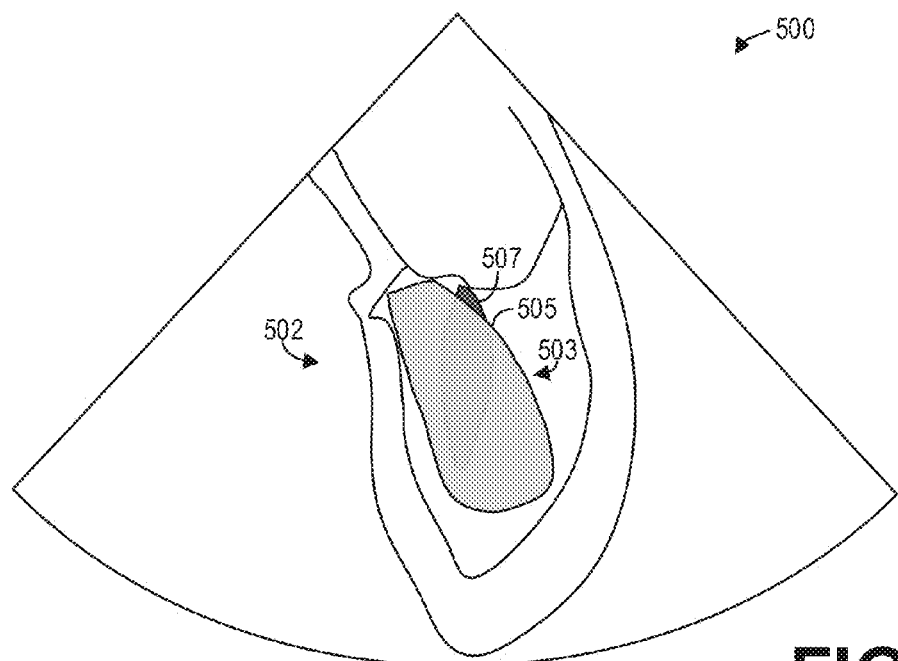
FIG. 5 shows an unprocessed ultrasound image according to an embodiment of the invention.
Figure 6:
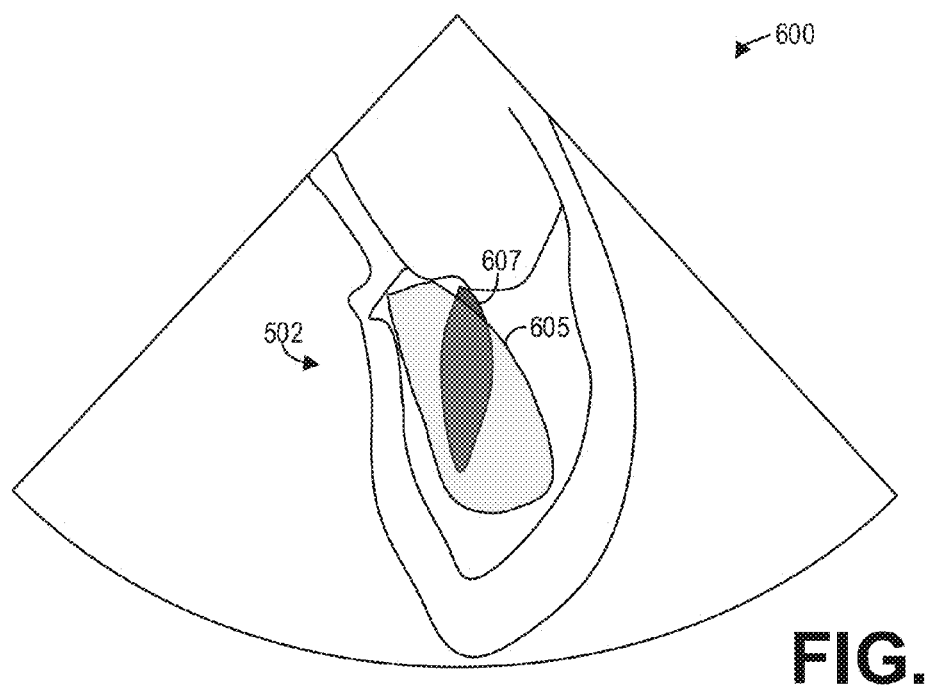
FIG. 6 shows a processed ultrasound image according to an embodiment of the invention.

As an illustrative example application of the methods and systems described herein, FIGS. 5 and 6 show an unprocessed ultrasound image 500 and a processed ultrasound image 600, respectively. In particular, the unprocessed ultrasound image 500 comprises the full, unadjusted flow data in a single mid-systolic frame. The image 500 depicts anatomic structures 502 (e.g., via a B-mode image) as well as blood flow 503 (e.g., via a color Doppler image superimposed on the B-mode image). The blood flow 503 includes regular blood flow 505 and a turbulent flow jet 507. Since the transparency (or opacity) of regular blood flow 505 is not adjusted, the turbulent flow jet 507 is obscured by the regular blood flow 505.

In contrast, the processed ultrasound image 600 is generated based on the same ultrasound dataset as the unprocessed ultrasound image 500, however the processed ultrasound image 600 displays flow voxels with, as a non-limiting example, only high variance over all velocities acquired over the whole systole. As a result, the regular blood flow 605 has an increased transparency with respect to the regular blood flow 505, since the regular blood flow 605 has low variance. In this way, the visualization of the turbulent flow jet 607 is improved.

A technical effect of the disclosure is the calculation of flow transparency values based on velocity, variance, time, and space. Another technical effect of the disclosure is the rendering of an ultrasound image comprising a single frame with turbulent blood flow visualized over time. Another technical effect of the disclosure is the display of an ultrasound image rendered with transparency values of each voxel determined based on velocity, variance, and spatial position of each voxel as well as the acquisition time of the voxel. Thus, another technical effect of the disclosure is an improved visualization of turbulent blood flow.

In one embodiment, a method comprises calculating transparency values for a plurality of voxels based on a variance value and a velocity value of each voxel and a time corresponding to acquisition of each voxel, and rendering an image with the calculated transparency values applied to the plurality of voxels. In a first example of the method, the transparency values are calculated based on a transparency transfer function that maps the variance value of a voxel, the velocity value of the voxel, and the time corresponding to the acquisition of the voxel to a transparency value to be applied to the voxel. In a second example of the method optionally including the first example, the transparency transfer function is selected from default transparency transfer functions. In a third example of the method optionally including one or more of the first and second examples, the method further comprises receiving a user adjustment of the transparency transfer function, and the calculation of the transparency values is performed with the user-adjusted transparency transfer function. In a fourth example of the method optionally including one or more of the first through third examples, the time corresponding to the acquisition of the voxel occurs within a time window selected by a user, and the transparency value to be applied to the voxel varies based on the temporal position of the time within the time window. In a fifth example of the method optionally including one or more of the first through fourth examples, transparency values of voxels acquired at times outside the time window are set to a minimum transparency value. The minimum transparency value may be, as a non-limiting example, full transparency, or may be established by a user such that flow voxels other than those of interest may still be visualized in the image. In a sixth example of the method optionally including one or more of the first through fifth examples, the time window is selected by the user by identifying a start time and an end time. In a seventh example of the method optionally including one or more of the first through sixth examples, the time window corresponds to a subset of a cardiac cycle, and the transparency value calculation is performed for all data within the subset of the cardiac cycle when the ultrasound data is acquired over multiple cardiac cycles. In an eighth example of the method optionally including one or more of the first through seventh examples, the rendered image comprises a single ultrasound frame wherein the plurality of voxels are integrated over the time window. In a ninth example of the method optionally including one or more of the first through eighth examples, the rendered image comprises a plurality of ultrasound frames to be displayed at a specified frame rate. In a tenth example of the method optionally including one or more of the first through ninth examples, the method further comprises transmitting the image to a display device for display to a user.

In another embodiment, a method comprises receiving a selection of a time window, calculating velocity values and variance values for a plurality of voxels within a volume of data acquired during the selected time window, calculating a transparency value for each of the plurality of voxels based on the calculated velocity value, the calculated variance value, and an acquisition time of each voxel, and displaying an image rendered with the calculated transparency values applied to the plurality of voxels. In a first example of the method, the method further comprises receiving a spatial selection indicating a physical region within the volume, wherein calculating the transparency value for each of the plurality of voxels is further based on a spatial position of each voxel, the spatial position located within the spatial selection. In a second example of the method optionally including the first example, calculating the transparency value for each of the plurality of voxels comprises inputting the calculated velocity value, the calculated variance value, and the acquisition time into a transparency transfer function which outputs the transparency value corresponding to the input. In a third example of the method optionally including the first and second examples, the method further comprises receiving a user adjustment of the transparency value after displaying the image, rendering a second image with the user adjusted transparency value, and displaying the second image. In a fourth example of the method optionally including one or more of the first through third examples, the selection of the time window comprises a selection of a start point and an end point within an echocardiogram.

In yet another embodiment, an ultrasound imaging system comprises: a transducer array adapted to transmit a plurality of ultrasound waves and receive a plurality of echoes; a display device configured to display an ultrasound image; and a processor communicatively coupled to the transducer array and the display device, the processor configured with computer-readable instructions in non-transitory memory that when executed cause the processor to: calculate transparency values for a plurality of voxels corresponding to the plurality of echoes based on a variance value, a velocity value, and a spatial position of each voxel in the plurality of voxels; render an image with the calculated transparency values applied to the plurality of voxels; and transmit the image to the display device for display to a user. In a first example of the system, calculating the transparency values for the plurality of voxels comprises inputting the calculated velocity value, the calculated variance value, and the spatial position of each voxel into a transparency transfer function which outputs a transparency value for each voxel based on the corresponding input. In a second example of the system optionally including the first example, an acquisition time of each voxel is further input to the transparency transfer function, and the transparency value output for each voxel is further based on the acquisition time. In a third example of the system optionally including one or more of the first and second examples, the system further comprises a user interface communicatively coupled to the processor and configured to facilitate input from the user, wherein the processor is further configured with computer-readable instructions in the non-transitory memory that when executed cause the processor to receive user adjustments of the transparency transfer function from the user interface, wherein the user adjustments comprise at least one adjustment of a relationship between the transparency value and the variance value, the velocity value, the acquisition time, and the spatial position. In a fourth example of the system optionally including one or more of the first through third examples, the processor is further configured with computer-readable instructions in the non-transitory memory that when executed cause the processor to, responsive to receiving a user adjustment of the transparency value after displaying the image, render a second image with the user-adjusted transparency value, and transmit the second image to the display device for display to the user. In a fifth example of the system optionally including one or more of the first through fourth examples, the rendered image comprises a single ultrasound frame wherein the plurality of voxels are integrated over time.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   calculating transparency values for a plurality of voxels based on a variance value and a velocity value of each voxel and a time corresponding to acquisition of each voxel; and
   rendering an image with the calculated transparency values applied to the plurality of voxels, wherein the calculated transparency values include different transparency values for two voxels with a same variance value and a same velocity value but acquired at different times.

2. The method of claim 1, wherein the transparency values are calculated based on a transparency transfer function that maps the variance value of a voxel, the velocity value of the voxel, and the time corresponding to the acquisition of the voxel to a transparency value to be applied to the voxel.

3. The method of claim 2, further comprising receiving a user adjustment of the transparency transfer function, and wherein the calculation of the transparency values is performed with the user-adjusted transparency transfer function.

4. The method of claim 2, wherein the time corresponding to the acquisition of the voxel occurs within a time window selected by a user, wherein the transparency value to be applied to the voxel varies based on a temporal position of the time within the time window, wherein the two voxels are acquired at the different times within the time window.

5. The method of claim 4, wherein transparency values of voxels acquired at times outside the time window are set to a minimum transparency value.

6. The method of claim 5, wherein the time window corresponds to a subset of a cardiac cycle, and wherein the transparency value calculation is performed for all data within the subset of the cardiac cycle when ultrasound data is acquired over multiple cardiac cycles.

7. The method of claim 4, wherein the rendered image comprises a single ultrasound frame wherein the plurality of voxels is integrated over the time window.

8. The method of claim 1, wherein the rendered image comprises a plurality of ultrasound frames to be displayed at a specified frame rate.

9. The method of claim 1, wherein a transparency value calculated for a particular voxel is further based on variance values, velocity values, and acquisition times of other voxels in the plurality of voxels.

10. A method, comprising:
    receiving a selection of a time window;
    calculating velocity values and variance values for a plurality of voxels within a volume of data acquired during the selected time window;
    calculating a transparency value for each of the plurality of voxels based on the calculated velocity value, the calculated variance value, and an acquisition time of each voxel; and
    displaying an image rendered with the calculated transparency values applied to the plurality of voxels, wherein the calculated transparency values include different transparency values for two voxels of the plurality of voxels, the two voxels including a same calculated velocity value, a same calculated variance value, and different acquisition times within the selected time window.

11. The method of claim 10, further comprising receiving a spatial selection indicating a physical region within the volume of data, wherein calculating the transparency value for each of the plurality of voxels is further based on a spatial position of each voxel, the spatial position located within the spatial selection, wherein two voxels in different spatial positions within the spatial selection have different transparency values, the two voxels in the different spatial positions acquired at a same time with a same variance value and a same velocity value.

12. The method of claim 10, wherein calculating the transparency value for each of the plurality of voxels comprises inputting the calculated velocity value, the calculated variance value, and the acquisition time into a transparency transfer function which outputs the transparency value corresponding to the input.

13. The method of claim 12, further comprising receiving a user adjustment of the transparency value after displaying the image, rendering a second image with the user-adjusted transparency value, and displaying the second image.

14. The method of claim 10, wherein the selection of the time window comprises a selection of a start point and an end point within an echocardiogram.

15. An ultrasound imaging system, comprising:
a transducer array adapted to transmit a plurality of ultrasound waves and receive a plurality of echoes;
a display device configured to display an ultrasound image; and
a processor communicatively coupled to the transducer array and the display device, the processor configured with computer-readable instructions in non-transitory memory that when executed cause the processor to:
calculate transparency values for a plurality of voxels corresponding to the plurality of echoes based on a variance value, a velocity value, and a spatial position of each voxel in the plurality of voxels, wherein the calculated transparency values include different transparency values for two voxels of the plurality of voxels, wherein the two voxels have a same variance value and a same velocity value but different spatial positions within a region of interest;
render an image with the calculated transparency values applied to the plurality of voxels; and
transmit the image to the display device for display to a user.

16. The system of claim 15, wherein calculating the transparency values for the plurality of voxels comprises inputting the calculated velocity value, the calculated variance value, and the spatial position of each voxel into a transparency transfer function which outputs a transparency value for each voxel based on the corresponding input.

17. The system of claim 16, wherein an acquisition time of each voxel is further input to the transparency transfer function, and wherein the transparency value output for each voxel is further based on the acquisition time.

18. The system of claim 16, further comprising a user interface communicatively coupled to the processor and configured to facilitate input from the user, wherein the processor is further configured with computer-readable instructions in the non-transitory memory that when executed cause the processor to receive user adjustments of the transparency transfer function from the user interface, wherein the user adjustments comprise at least one adjustment of a relationship between the transparency value and the variance value, the velocity value, an acquisition time, and the spatial position.

19. The system of claim 18, wherein the processor is further configured with computer-readable instructions in the non-transitory memory that when executed cause the processor to, responsive to receiving a user adjustment of the transparency value after displaying the image, render a second image with the user-adjusted transparency value, and transmit the second image to the display device for display to the user.

20. The system of claim 15, wherein the rendered image comprises a single ultrasound frame wherein the plurality of voxels is integrated over time.

* * * * *